(12) United States Patent
Stallard et al.

(10) Patent No.: US 8,616,210 B2
(45) Date of Patent: Dec. 31, 2013

(54) PORTS CAP FOR MASK ASSEMBLY

(75) Inventors: Philip Thomas Stallard, Denistone East (AU); Mark Bertinetti, Lane Cove (AU); Scott Alexander Howard, Harbord (AU)

(73) Assignee: ResMed Limited, Bella Vista (AU)

( * ) Notice: Subject to any disclaimer, the term of this patent is extended or adjusted under 35 U.S.C. 154(b) by 1185 days.

(21) Appl. No.: 11/826,201

(22) Filed: Jul. 12, 2007

(65) Prior Publication Data

US 2008/0066757 A1 Mar. 20, 2008

Related U.S. Application Data

(60) Provisional application No. 60/830,097, filed on Jul. 12, 2006, provisional application No. 60/838,371, filed on Aug. 18, 2006.

(51) Int. Cl.
| | |
|---|---|
| *A61M 16/06* | (2006.01) |
| *A62B 18/02* | (2006.01) |
| *F16L 55/11* | (2006.01) |
| *F16L 55/115* | (2006.01) |

(52) U.S. Cl.
USPC ............ 128/206.21; 128/205.25; 128/206.28; 138/89; 138/91; 137/800

(58) Field of Classification Search
USPC ................. 128/205.25, 206.21–207.13, 912; 137/800; 215/295, 296, 298, 305, 200, 215/205, 211, 224, 355–364; 222/153.01, 222/153.02, 153.05–153.07, 546, 563; 138/89, 91
See application file for complete search history.

(56) References Cited

U.S. PATENT DOCUMENTS

| | | | | | |
|---|---|---|---|---|---|
| 3,247,997 | A | * | 4/1966 | Bozek | 220/272 |
| 3,335,720 | A | * | 8/1967 | Aileo | 128/866 |
| 3,635,217 | A | * | 1/1972 | Potash | 128/201.19 |
| 4,344,472 | A | * | 8/1982 | Larkin et al. | 220/266 |
| 4,841,963 | A | * | 6/1989 | Vandeputte | 128/202.15 |
| 5,057,093 | A | * | 10/1991 | Clegg et al. | 604/535 |
| 5,382,242 | A | * | 1/1995 | Horton et al. | 604/256 |
| 5,513,768 | A | * | 5/1996 | Smith | 220/259.2 |
| 6,439,230 | B1 | * | 8/2002 | Gunaratnam et al. | 128/206.21 |
| 6,615,829 | B2 | * | 9/2003 | Horn et al. | 128/202.15 |
| 2005/0092379 | A1 | * | 5/2005 | Pfadt et al. | 137/800 |
| 2005/0172969 | A1 | * | 8/2005 | Ging et al. | 128/206.24 |

FOREIGN PATENT DOCUMENTS

WO PCT/AU2006/000037 7/2006
WO PCT/AU2006/000031 4/2007

OTHER PUBLICATIONS

U.S. Appl. No. 29/261,578, filed Jun. 2006, Chu et al.
U.S. Appl. No. 29/251,704, filed Jan. 2006, Stallard.

* cited by examiner

*Primary Examiner* — Justine R Yu
*Assistant Examiner* — Valerie L Skorupa
(74) *Attorney, Agent, or Firm* — Nixon & Vanderhye, P.C.

(57) ABSTRACT

A ports cap for a mask assembly includes two closure portions adapted to seal respective ports of the mask assembly, a bridge piece that joins the two closure portions, and two gripping tabs extending outwardly from respective closure portions. Each gripping tab includes one or more ribs on at least one side thereof.

40 Claims, 14 Drawing Sheets

PORTS CAP FOR MASK ASSEMBLY

CROSS-REFERENCE TO RELATED APPLICATIONS

This application claims the benefit of U.S. Provisional Patent Application No. 60/830,097, filed Jul. 12, 2006, and 60/838,371, filed Aug. 18, 2006, each of which is incorporated herein by reference in its entirety.

FIELD OF THE INVENTION

The invention relates to a ports cap for a mask assembly used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE INVENTION

Mask assemblies used in the treatment of SDB may comprise a nasal mask, designed to fit over a patient's nose, or a full face mask designed to fit over the nose and mouth of the patient. In both cases, the mask is held in position by headgear.

The mask generally comprises a relatively rigid shell, termed a frame, which defines a rearwardly opening cavity covering the patient's nose and/or mouth and a soft portion, termed a cushion, which contacts and seals against the patient in a preferably comfortable manner.

The air or other breathable gas is supplied by a blower and passed along a flexible conduit to the mask. The conduit is typically of relatively large bore, for example approximately 2 cm diameter, with the mask frame having a gas inlet of comparable diameter.

In addition to the gas inlet, the mask may also have $CO_2$ washout vents and one or more small diameter ports through which supplemental oxygen may be introduced or pressure measurements made. The ports typically comprise a pair of cylindrical connectors molded into the mask frame, usually projecting forward from the front surface of the frame. The mask ports typically also include a cap which prevents leakage of air from the mask when the port is not in use.

Depending on the part construction and the relative diameters of the port and the tubing which supplies supplemental oxygen, the port may function as a male or a female connector. The Mirage® nasal mask (ResMed Ltd.) is a generally triangular mask with a gas inlet tube extending upwards from its apex. The two ports of that mask are located in the front of the gas inlet tube just above the patient's eye level, between a pair of shield projections. A single cap of silicone rubber covers both ports, and has tabs at either end to facilitate removal by pulling on the tabs in a direction away from patient's face.

There is a need for ports which are conveniently located on the mask, which are protected from accidental breakage and which do not foul tubing. There is a need for a corresponding ports cap which is sufficiently large so as to be easy to handle and which is not so small as to be easily lost.

SUMMARY OF THE INVENTION

One aspect of the invention relates to a ports cap for a mask assembly. The ports cap includes two closure portions adapted to seal respective ports of the mask assembly, a bridge piece that joins the two closure portions, and two gripping tabs extending outwardly from respective closure portions. Each gripping tab includes one or more ribs on at least one side thereof.

Another aspect of the invention relates to a ports cap for a mask assembly. The ports cap includes two closure portions adapted to seal respective ports of the mask assembly, a bridge piece that joins the two closure portions, and two gripping tabs extending outwardly from respective closure portions. Each gripping tab extends from a lateral side of the respective closure portion such that it extends generally parallel with the bridge piece.

Another aspect of the invention relates to a port cap for a mask assembly. The port cap includes a closure portion adapted to seal a port of the mask assembly and a gripping tab extending outwardly from the closure portion. The gripping tab includes one or more ribs on at least one side thereof.

Another aspect of the invention relates to a port cap for a mask assembly. The port cap includes a closure portion adapted to seal a port of the mask assembly and a gripping tab extending outwardly from the closure portion. The gripping tab extends from a lateral side of the closure portion.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1A:
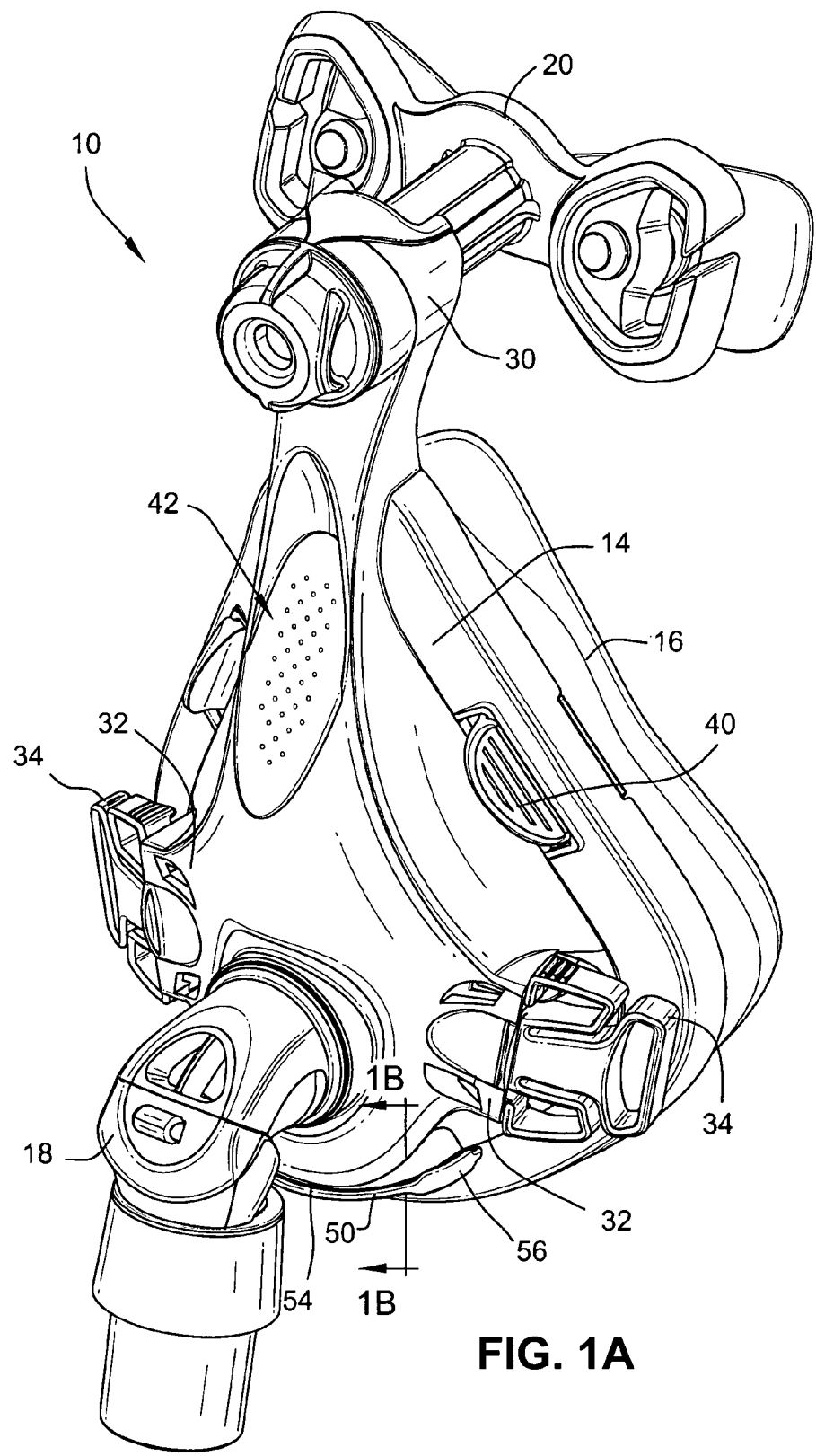
FIGS. 1A-4 are various views of a full facial mask assembly including a ports cap according to an embodiment of the present invention.

The following includes a description of a ports cap according to an embodiment of the present invention. In the illustrated embodiment, the ports cap is adapted to be removably attached to a frame of a mask assembly of the type described below. The general operation of the embodiment described herein is substantially similar to the operation of the embodiments detailed in U.S. Pat. No. 6,439,230, which is incorporated herein by reference in its entirety.

Mask Assembly

FIGS. 1A-4 illustrate an exemplary embodiment of a full facial mask assembly ("FMA") 10 including a ports cap 50 according to an embodiment of the present invention. As illustrated, the mask assembly 10 includes a frame 14, a cushion 16 provided to the frame 14 and adapted to form a seal with the patient's face, an elbow assembly 18 provided to the frame 14 and adapted to be connected to an air delivery tube (not shown) that delivers breathable gas to the patient, and a forehead support 20 to provide a support and stability mechanism between the mask assembly 10 and the patient's forehead. A headgear assembly (not shown) may be removably attached to the frame 14 and the forehead support 20 to maintain the mask assembly 10 in a desired adjusted position on the patient's face.

Further details and embodiments of such mask assemblies are disclosed in PCT Application Nos. PCT/AU2006/000031 and PCT/AU2006/000037, and Design application Ser. No. 29/261,578, filed Jun. 16, 2006 and entitled "Patient Interface and Components Therefore", each of which is incorporated herein by reference in its entirety. While the ports cap 50 is described as being used with a mask assembly 10 of the type described above, it may be adapted for use with other suitable mask assemblies. That is, the mask assembly 10 is merely exemplary, and the ports cap 50 may be adapted for use with any suitable mask assembly, e.g., a full-face (oro-nasal) mask, a mouth (oro) mask, or a nasal mask.

Mask Frame

Figure 5:
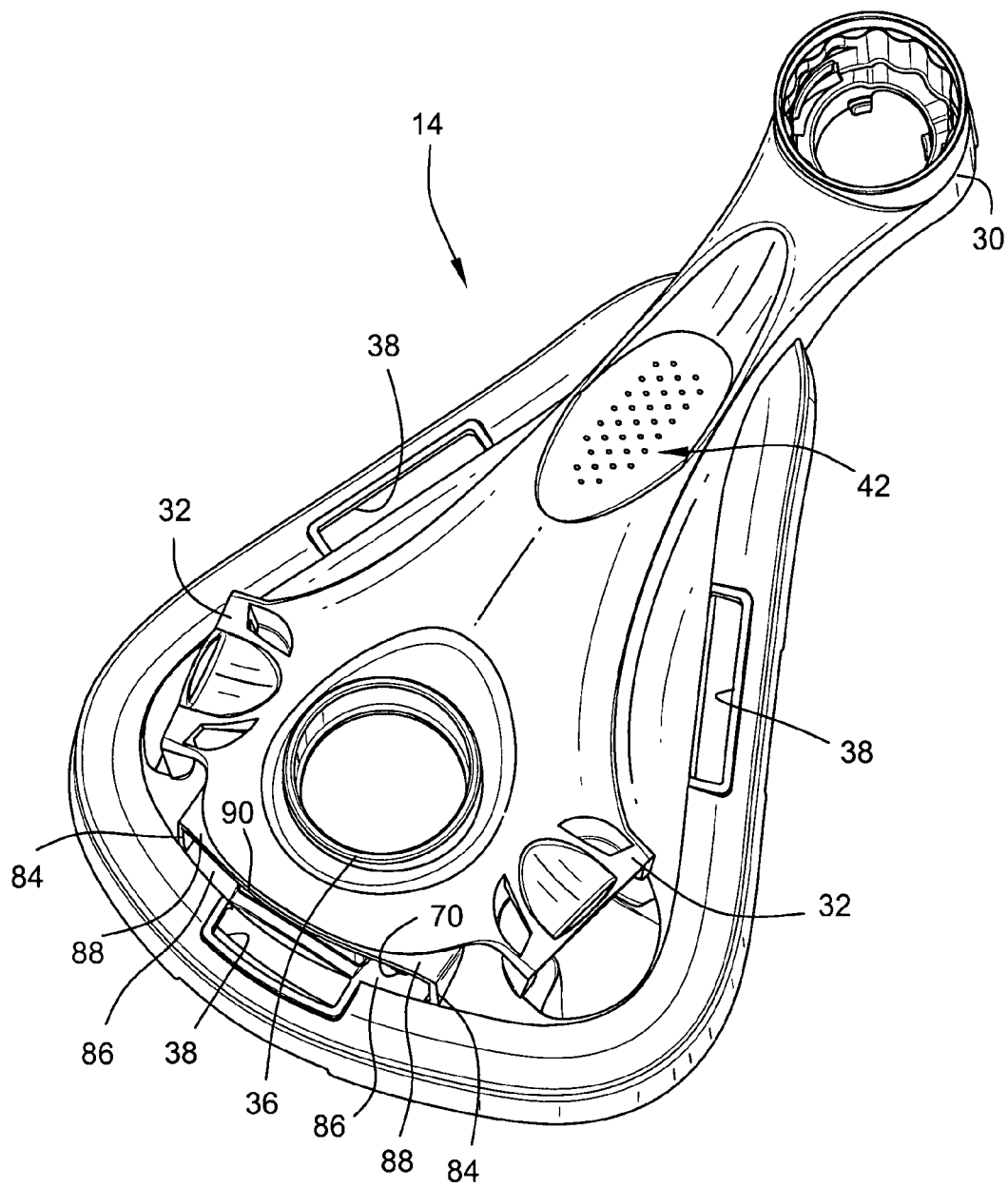
FIGS. 5-7 are various views of a frame of the full facial mask assembly shown in FIGS. 1A-4.
Figure 6:
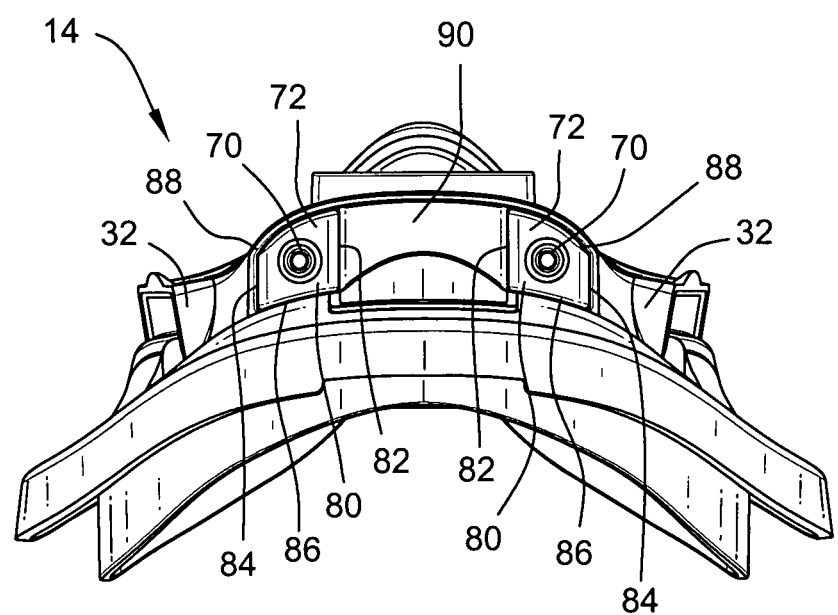
Figure 7:
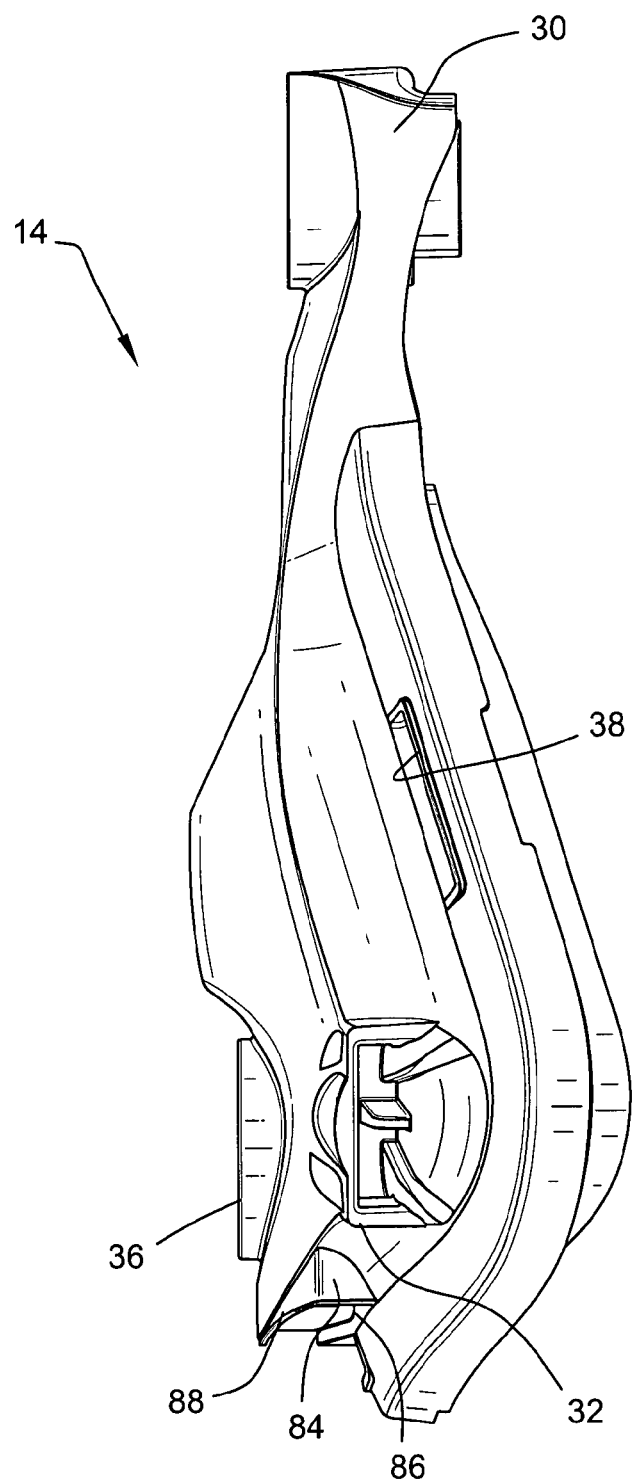
Figure 8:
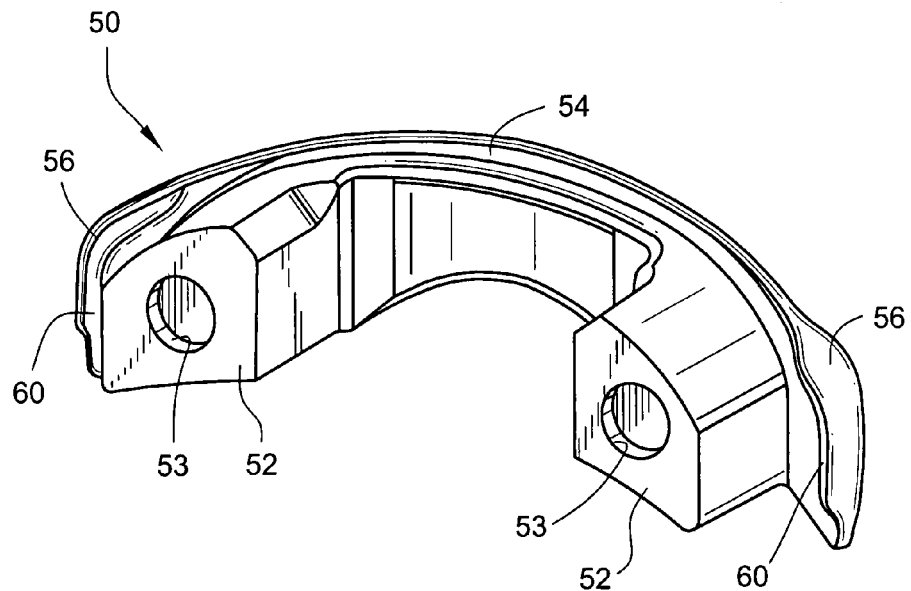
FIGS. 8-14 are various views of the ports cap shown in FIGS. 1A-4 removed from the full facial mask assembly.
Figure 9:
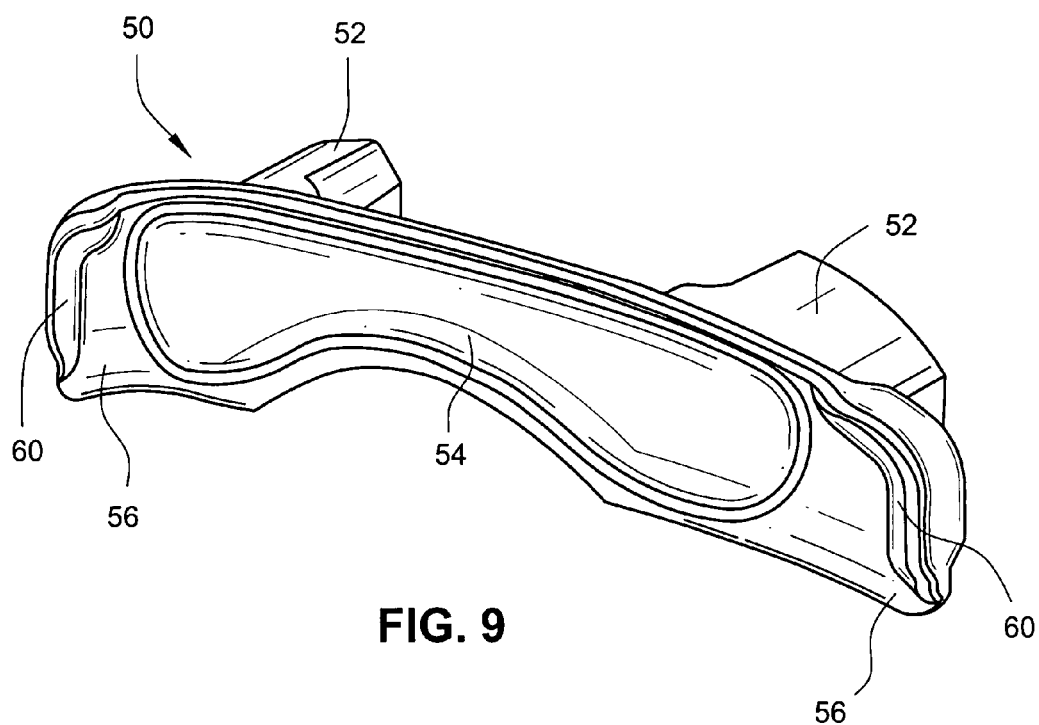
Figure 10:
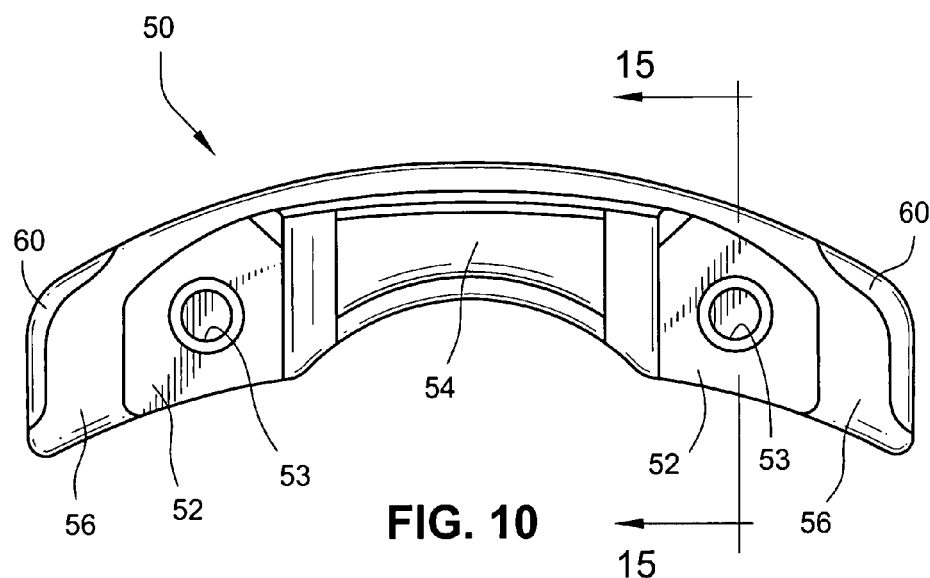
Figure 11:
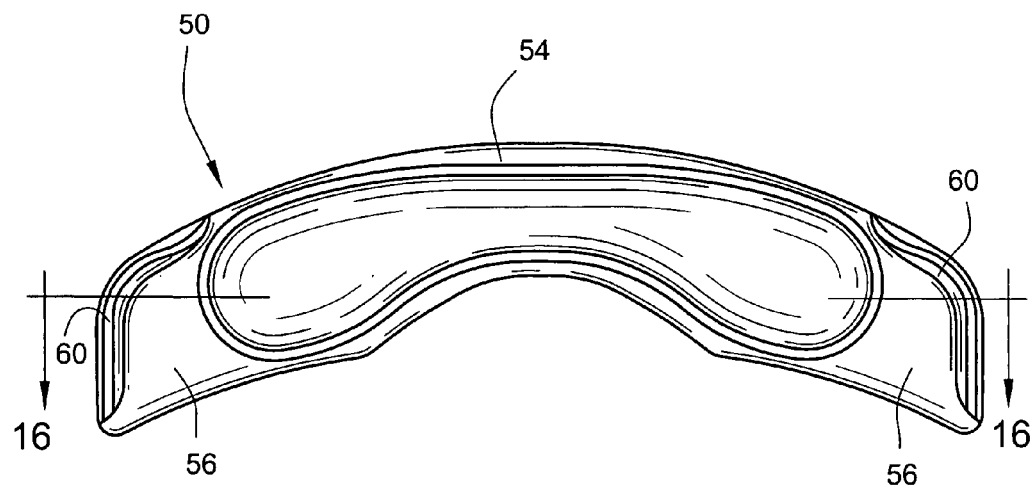
Figure 12:
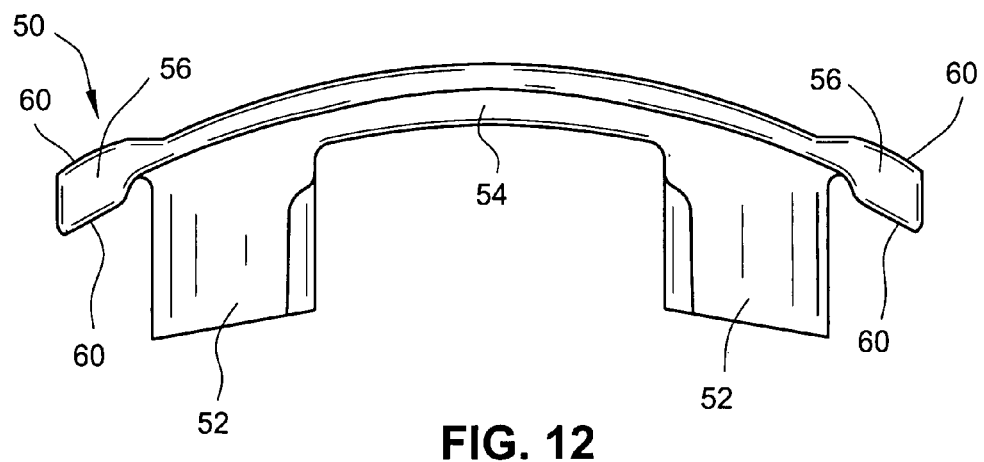
Figure 13:
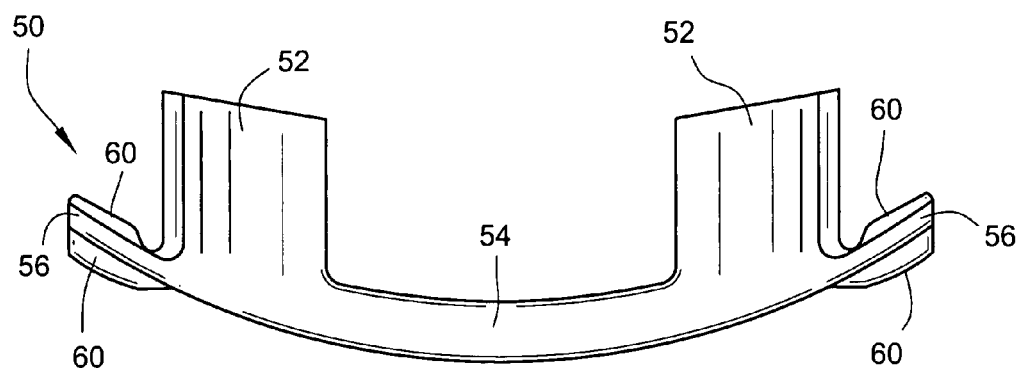
Figure 14:
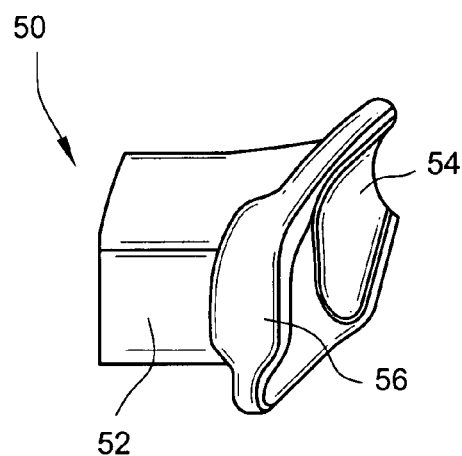

FIGS. 5-7 illustrate the frame 14 isolated from the other components of the mask assembly 10. As illustrated, the frame 14 includes an upper support member 30 adapted to support the forehead support 20, lower headgear clip receptacles 32 adapted to be engaged with clips 34 (e.g., see FIGS. 1A-4) provided to straps of a headgear assembly (not shown), and an annular elbow connection seal 36 adapted to engage the elbow assembly 18. Also, the top wall of the frame 14 includes a plurality of slots 38 therethrough, e.g., three slots, that are adapted to engage a cushion clip 40 (portions of clip 40 shown in FIGS. 1A-4) that retains the cushion 16 to the frame 14. In addition, the frame 14 includes a vent assembly 42 for gas washout. In an embodiment, the frame 14 is molded in one-piece with polycarbonate.

As best shown in FIG. 6, the frame includes two ports 70 located in recesses 72 in the base of the frame 14. These recesses 72 are positioned in between the lower headgear clip receptacles 32. The ports 70 are positioned so that in use, oxygen or other breathable gas can be delivered close to the patient's nares. Each port 70 is formed as a tubular spigot that forms the male connector onto which small bore tubing supplying, for example, oxygen, may be attached.

In the illustrated embodiment, each recess 72 includes an asymmetrical shape bounded by upper wall 80 that supports the port 70, inner side wall 82, outer side wall 84, rear wall 86, and front wall 88, and is open at its bottom end. The front wall 88 may be formed as a continuation of a front wall portion of the frame 14. The walls 82, 84, 86, 88 of the recess 72 are spaced from the port 70 by a sufficient distance to allow a small bore oxygen tube to be pushed onto the port 70, and also to allow closure portions 52 of the ports cap 50 (see FIGS. 8-16) to be received therewithin.

The base of the frame 14 may also include a shallow bridging recess 90 for receiving at least a portion of the bridge piece 54 joining the two closure portions 52 of the ports cap 50.

Figure 3A:
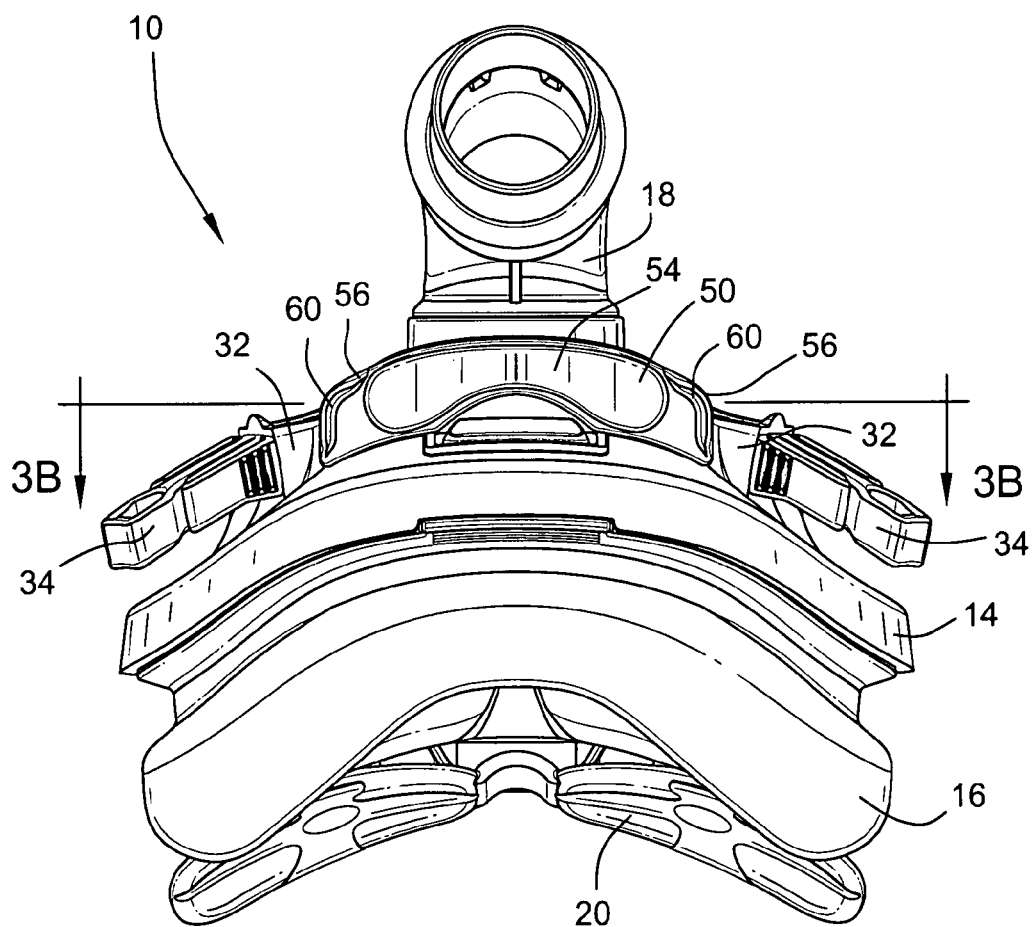
Figure 3B:
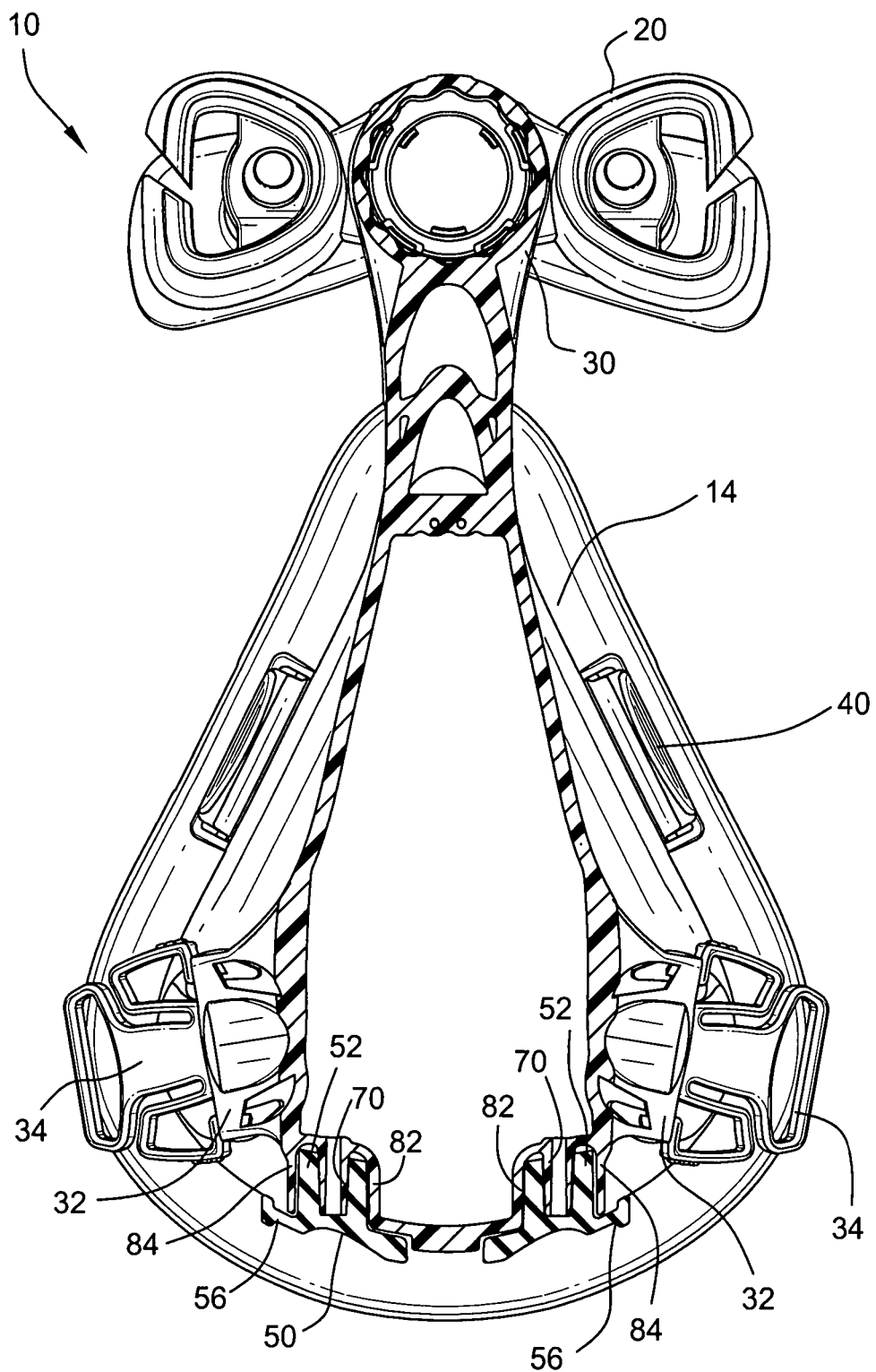
Figure 4:
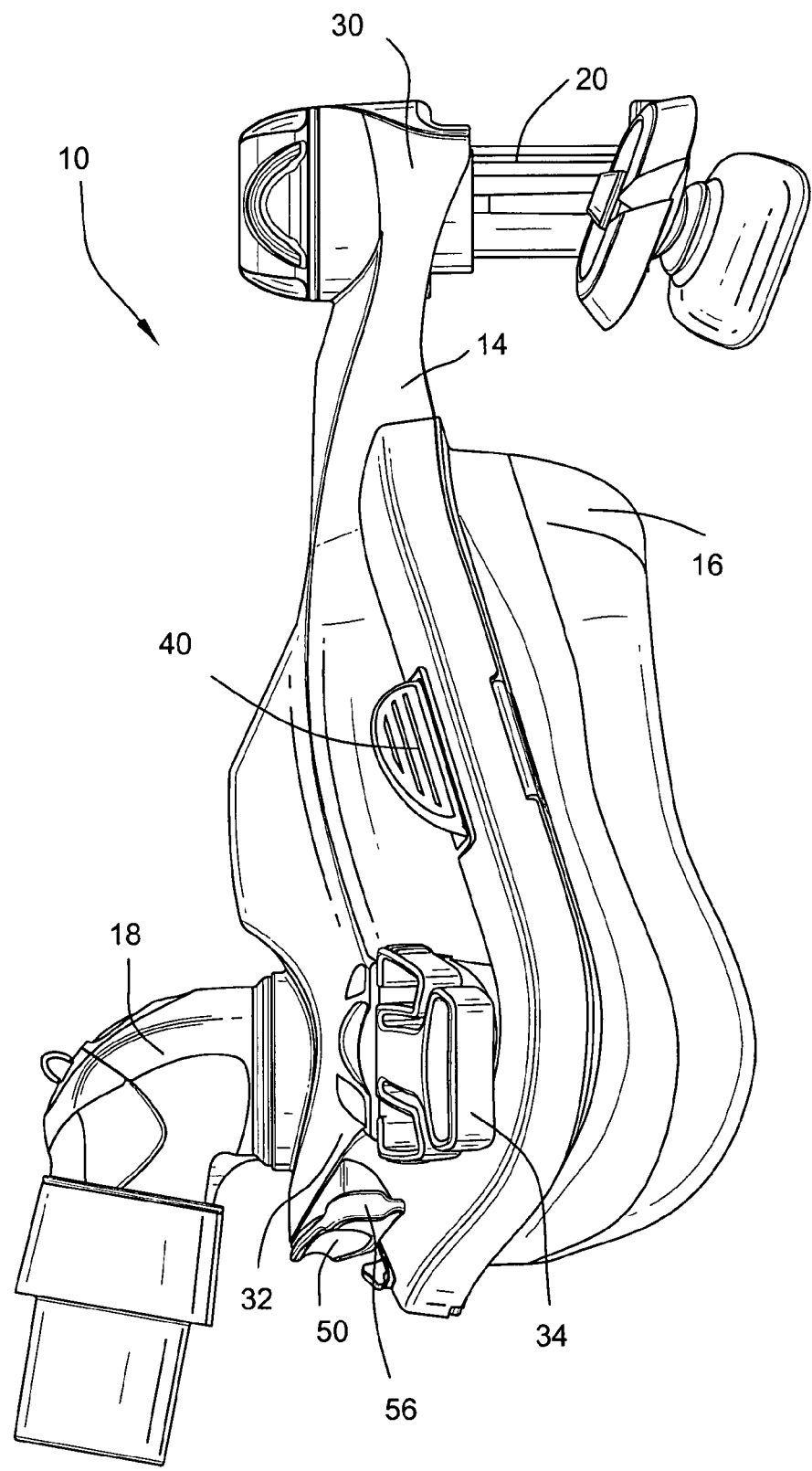

As best shown in FIG. 3B, gripping tabs 56 of the ports cap 50 extend beyond or overhang respective outer side walls 84 for gripping by the user. Pulling downwards on the tab 56 will remove the respective closure portion 52 from its port or spigot 70 to allow attachment of an oxygen tube or a tube leading to a measurement device.

Ports Cap

FIGS. 8-16 illustrate the ports cap 50 according to an embodiment of the present invention. As illustrated, the ports cap includes the two closure portions 52, the bridge piece 54 joining the two closure portions 52, and the two gripping tabs 56 extending outwardly from respective closure portions 52.

In an embodiment, the ports cap 50 is formed of a relatively soft elastomeric material such as silicone.

Each closure portion 52 includes an opening 53 adapted to receive the respective port or spigot 70 on the frame 14 in use. In an embodiment, the opening 53 seals the port 70 and retains the closure portion 52 on the port 70, e.g., the surfaces defining the opening 53 engage the port 70 to provide a seal and retain the closure portion 52 on the port 70. The walls 82, 84, 86, 88 of the recess 72 may be spaced from the closure portion 52 (e.g., the walls 82, 84, 86, 88 allow clearance between themselves and the closure portion 52) and/or the walls 82, 84, 86, 88 may engage the closure portion 52.

Figure 1B:
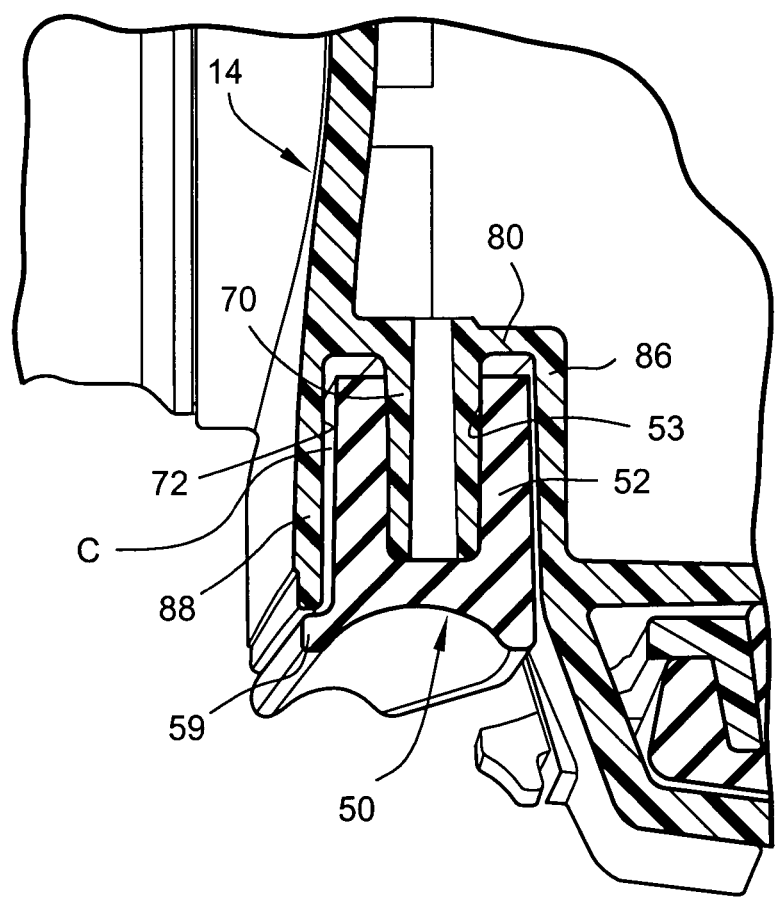
Figure 2:
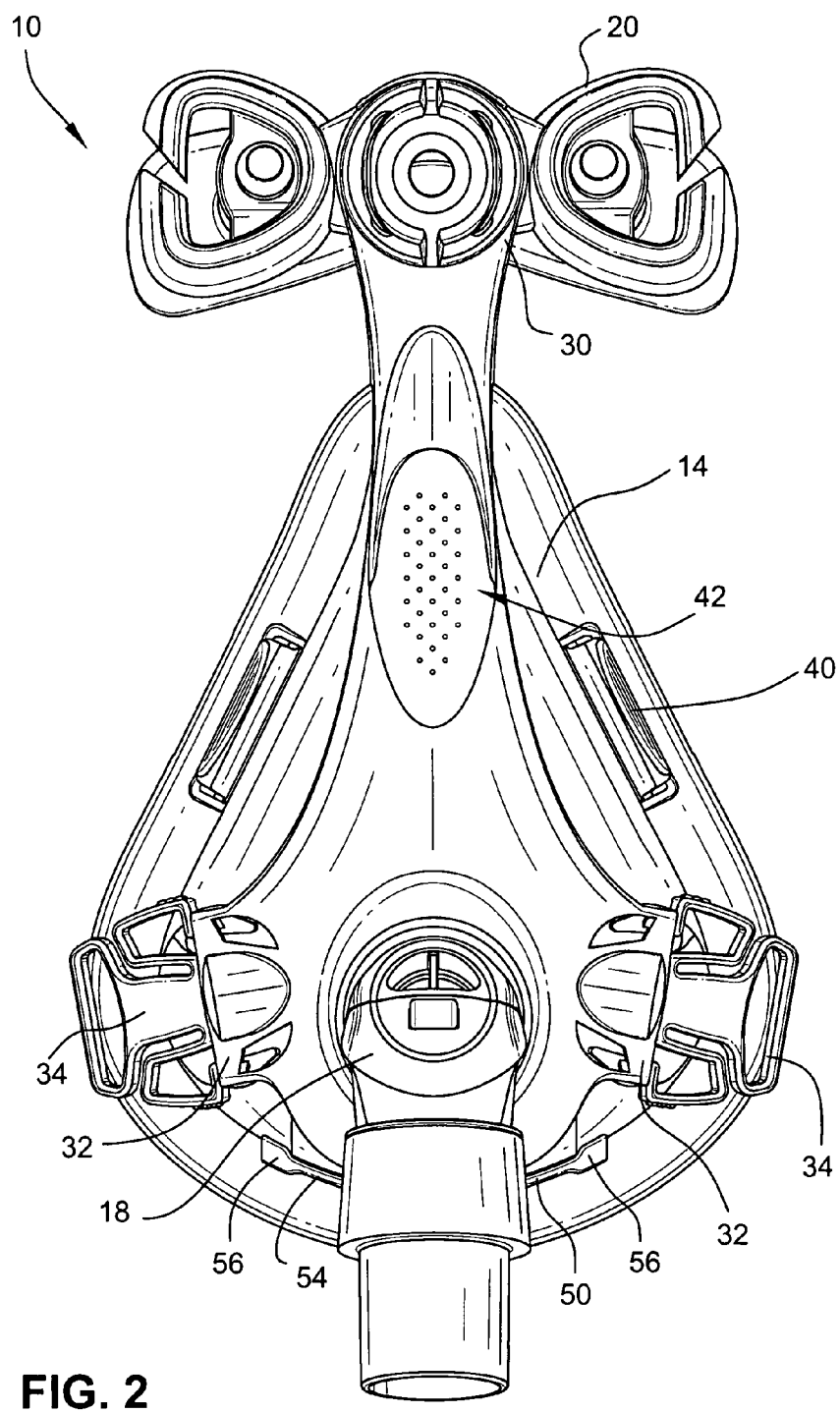

For example, FIG. 1B is a cross-sectional view illustrating an embodiment of the interface between the ports cap 50 and a port 70 on the frame 14. As illustrated, interference is provided between the opening 53 of the ports cap 50 and the port 70 to provide a seal and retain the closure portion 52 on the port 70. In addition, clearance C is provided between the closure portion 52 and at least one of the walls 82, 84, 86, 88 of the recess 72. Also, the ports cap 50 includes a lip 59 structured to extend over the front wall 88 such that it is substantially flush with a front surface of the front wall 88.

In an alternative embodiment, the walls 82, 84, 86, 88 may be used to provide a seal and retain the closure portion 52 within the recess 72, e.g., the exterior surfaces of the closure portion 52 engage the walls 82, 84, 86, 88 to seal and retain the closure portion 52.

Figure 15:
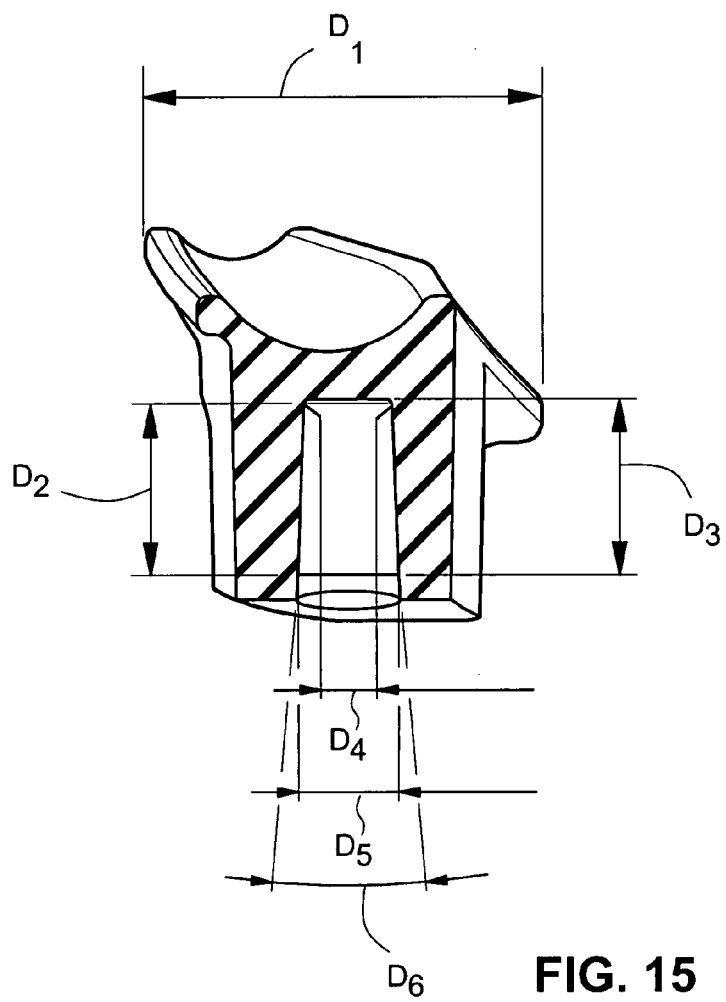
FIG. 15 is a cross-sectional view through line 15-15 of FIG. 10 and showing exemplary dimensions of an embodiment.

In an embodiment, the opening 53 may have sloped side walls, e.g. see FIG. 15. In addition, each closure portion 52 includes an asymmetrical shape that corresponds to the asymmetric shape of the recesses 72. This arrangement reduces the likelihood that the ports cap 50 will be incorrectly assembled.

In the illustrated embodiment, the gripping tabs 56 extend from respective lateral sides of the closure portions 52, e.g., extend generally parallel (e.g., coplanar or colinear) with the bridge piece 54. This arrangement facilitates removal of the ports cap 50 from the frame 14 via the tabs 56. In addition, each gripping tab 56 includes one or more ribs 60 on the top and/or bottom surfaces thereof, which allows each gripping tab 56 to be found easier and to be easier held, e.g., for disassembly.

In the illustrated embodiment, the rib 60 is in the general form of an "L" or "C". However, the rib may be formed in other shapes as well, such as a linear segment that is formed along a border of the tab 56. Furthermore, the rib may be in the form of a bead. In addition or in the alternative to the rib, the tab may include a textural, tacky, and/or roughened surface that improves gripability and provides a tactile cue that the patient/clinician has grasped the correct part of the tab.

Further, the ports cap 50 is relatively large to aid assembly and disassembly. Specifically, the ports cap 50 is easier to handle, easier to find if dropped, and the gripping tabs 56 are relatively large and easily found for disassembly.

Figure 16:
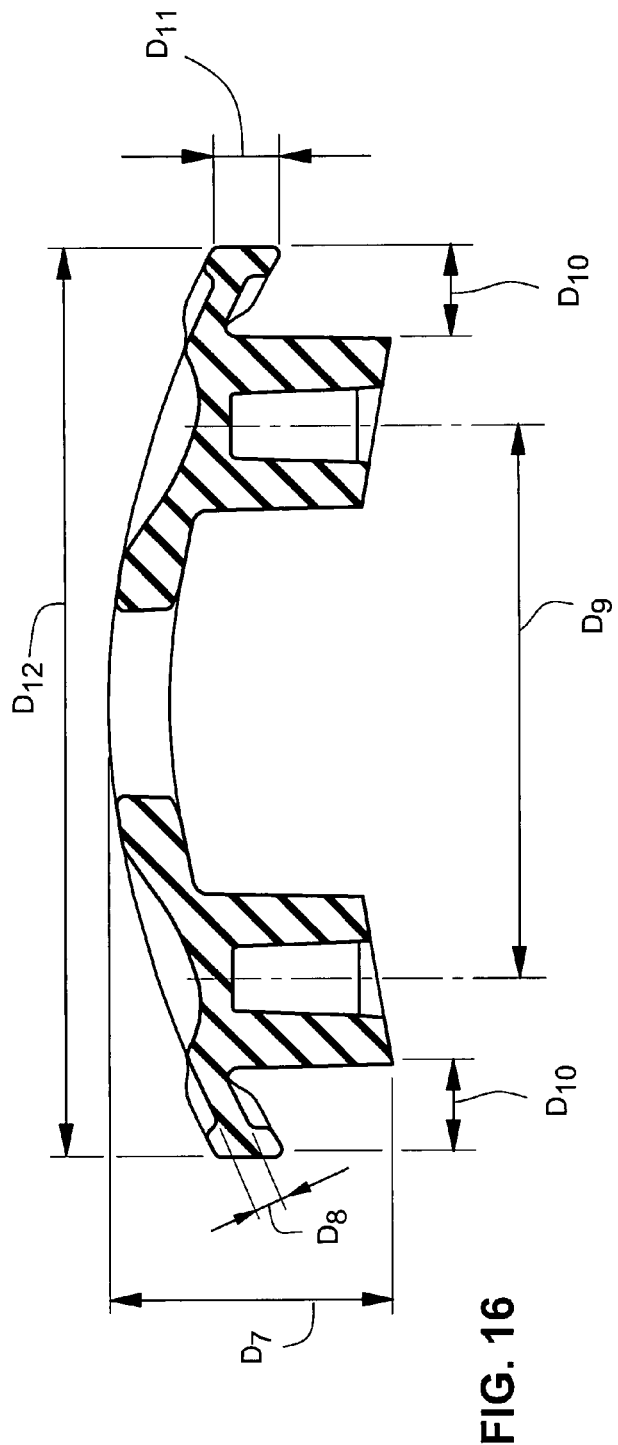
FIG. 16 is a cross-sectional view through line 16-16 of FIG. 11 and showing exemplary dimensions of an embodiment.

In an embodiment of the ports cap 50, as shown in FIGS. 15 and 16, $D_1$ may be in the range of 7-15 mm, e.g., preferably 11 mm, $D_2$ may be about 7 mm, $D_3$ may be about 7-8 mm, $D_4$ may be about 3-4 mm, $D_5$ may be about 4-5 mm, $D_6$ may be about 10°, $D_7$ may be in the range of 10-24 mm, e.g., preferably 16 mm, $D_8$ may be about 1.5 mm, $D_9$ may be about 30-31 mm, $D_{10}$ may be in the range of 2-42 mm, e.g., preferably 6 mm, $D_{11}$ may be in the range of 0.5-6 mm, e.g., preferably 1.5 mm, and $D_{12}$ may be in the range of 16-100 mm, e.g., preferably 51 mm. Although specific dimensions and ranges of the ports cap are indicated, it is to be understood that these dimensions and ranges are merely exemplary and other dimensions and ranges are possible depending on application. For example, the exemplary dimensions may vary by 10-20% or more or less depending on application.

In an alternative embodiment, the port may be in the form of a female connector and the closure portions 52 of the ports cap 50 may act as a male connector, e.g., no openings 53 needed, to seal the port, as described in U.S. Pat. No. 6,439,230.

In another embodiment, a port cap may include a single closure portion 52 with a gripping tab 56, e.g., for sealing a single port provided to the mask frame. In such an arrangement, the bridge piece may not be provided at all.

Figure 17:
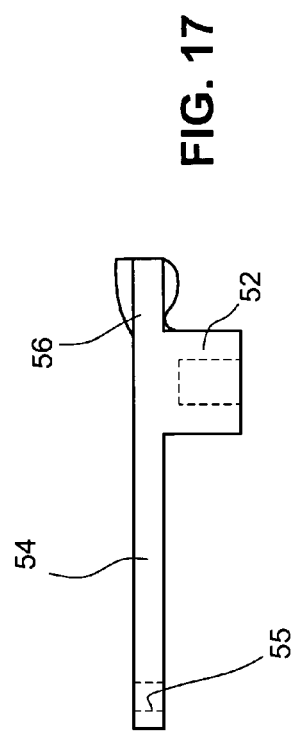
FIG. 17 is a schematic view of a ports cap according to another embodiment of the present invention.

In yet another embodiment, as shown in FIG. 17, a port cap may include a single closure portion 52, a bridge piece 54, and a gripping tab 56. In such an arrangement, the bridge piece 54 may include an opening 55 adapted to engage an anchor provided to the frame 14, e.g., one of the ports 70 may be replaced with an anchor adapted to engage the opening 55 in the bridge piece 54.

Other suitable arrangements of the ports cap are also possible depending on application, e.g., more than two closure portions.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A mask assembly comprising:
   a frame including two ports each comprising a tubular spigot that forms a male connector; and
   a ports cap comprising:
      two closure portions adapted to seal respective ports of the mask assembly, each closure portion being adapted to receive and seal a respective spigot on the respective port;
      a bridge piece that joins the two closure portions; and
      two gripping tabs extending outwardly from respective closure portions, each gripping tab including one or more ribs on an outer surface of at least one side thereof,
      wherein each gripping tab extends from a lateral side of the respective closure portion such that it extends generally parallel with the bridge piece,
      wherein, in a side view in which the closure portions extend downwardly from the bridge piece, the bridge piece and gripping tabs extend along an arc configured to correspond to a curvature of the frame, and
      wherein the bridge piece and the two gripping tabs extend from similar ends of the closure portions.

2. The mask assembly according to claim 1, wherein the ports cap is formed of a relatively soft elastomeric material.

3. The mask assembly according to claim 1, wherein each closure portion includes an opening adapted to receive a respective port.

4. The mask assembly according to claim 3, wherein surfaces defining the opening are adapted to engage the port to provide a seal and retain the closure portion on the port.

5. The mask assembly according to claim 1, wherein each closure portion includes an asymmetrical shape.

6. The mask assembly according to claim 1, wherein the one or more ribs are provided along a free end of the gripping tab to enhance gripping of the gripping tab at least for disassembly of the closure portion from the respective port.

7. The mask assembly according to claim 1, wherein the gripping tab includes a rib along both sides thereof.

8. The mask assembly according to claim 1, wherein each closure portion includes an indentation along the end from which the gripping tab extends.

9. The mask assembly according to claim 1, wherein the bridge piece and gripping tabs extend along an arc.

10. The mask assembly according to claim 1, wherein in use the ports cap is constructed and arranged to be pulled downwards and laterally with respect to the mask assembly to remove the respective closure portion from a sealing relationship with the respective spigot.

11. A ports cap for a mask assembly, the ports cap comprising:
    two closure portions adapted to seal respective ports of the mask assembly;
    a bridge piece that joins the two closure portions; and
    two gripping tabs extending outwardly from respective closure portions, each gripping tab extending from a lateral side of the respective closure portion such that it extends generally parallel with the bridge piece,
    wherein, in a side view in which the closure portions extend downwardly from the bridge piece, the bridge piece and gripping tabs extend along an arc configured correspond to a curvature of a mating portion of a frame of the mask assembly, and further wherein in use the ports cap is constructed and arranged to be pulled downwards and laterally with respect to the mask assembly to remove a respective closure portion from a sealing relationship with the respective port.

12. A mask assembly comprising:
    a frame including two ports; and
    a ports cap according to claim 11.

13. The mask assembly according to claim 12, wherein each said port is located in a recess in a base of the frame.

14. The mask assembly according to claim 13, wherein each closure portion includes an opening that receives a respective port, and surfaces defining the opening engage the port to provide a seal and retain the closure portion on the port within the recess.

15. The mask assembly according to claim 13, wherein the recess is bounded by a plurality of walls, and the walls engage the closure portion to provide a seal and retain the closure portion within the recess.

16. The mask assembly according to claim 13, wherein each recess includes an asymmetrical shape.

17. The mask assembly according to claim 12, wherein each port is formed as a tubular spigot.

18. The mask assembly according to claim 12, wherein each said gripping tab of the ports cap extends beyond or overhangs respective outer side walls of the recess in use.

19. The mask assembly according to claim 12, wherein each said gripping tab of the ports cap extends toward sides of the frame in use.

20. The ports cap according to claim 11, wherein each tab is wider than at least a portion of the bridge piece.

21. A port cap for a mask assembly, the port cap comprising:
   a closure portion adapted to seal a port of the mask assembly; and
   a gripping tab extending outwardly from the closure portion, the gripping tab including one or more ribs on an outer surface of at least one side thereof,
   wherein the closure portion includes a continuous outer surface including an exposed indented portion, the gripping tab being directly adjacent the indented portion and extending from the indented portion.

22. The port cap according to claim 21, further comprising a bridge piece that extends from the closure portion, the bridge piece including an opening adapted to engage an anchor provided to the mask assembly.

23. The port cap according to claim 21, wherein the port cap is formed of a relatively soft elastomeric material.

24. The port cap according to claim 21, wherein the closure portion includes an opening adapted to receive a port.

25. The port cap according to claim 24, wherein surfaces defining the opening are adapted to engage the port to provide a seal and retain the closure portion on the port.

26. The port cap according to claim 21, wherein the closure portion includes an asymmetrical shape.

27. The port cap according to claim 21, wherein the gripping tab extends from a lateral side of the closure portion.

28. A mask assembly comprising:
   a frame including a port; and
   a port cap according to claim 21.

29. The port cap according to claim 21, wherein the one or more ribs are provided along a free end of the gripping tab to enhance gripping of the gripping tab at least for disassembly of the closure portion from the port.

30. The port cap according to claim 21, wherein the gripping tab includes a rib along both sides thereof.

31. A port cap for a mask assembly, the port cap comprising:
   two closure portions adapted to seal respective ports of the mask assembly;
   a bridge piece that joins the two closure portions, the bridge piece extending generally along an arc in a first direction between the two closure portions and
   a gripping tab extending outwardly from at least one of the closure portions, the gripping tab extending from a lateral side of the at least one closure portion along the arc in the first direction,
   wherein the gripping tab includes a rib along outer surfaces on both sides thereof, each rib provided along a free end of the gripping tab to enhance gripping of the gripping tab at least for disassembly of the closure portion from the port.

32. A mask assembly comprising:
   a frame including a port; and
   a port cap according to claim 31.

33. The mask assembly according to claim 32, wherein the port is located in a recess in a base of the frame.

34. The mask assembly according to claim 33, wherein the closure portion includes an opening that receives the port, and surfaces defining the opening engage the port to provide a seal and retain the closure portion on the port within the recess.

35. The mask assembly according to claim 33, wherein the recess is bounded by a plurality of walls, and the walls engage the closure portion to provide a seal and retain the closure portion within the recess.

36. The mask assembly according to claim 33, wherein the recess includes an asymmetrical shape.

37. The mask assembly according to claim 32, wherein the port is formed as a tubular spigot.

38. The mask assembly according to claim 32, wherein the gripping tab of the port cap extends beyond or overhangs an outer side wall of the recess in use.

39. The mask assembly according to claim 32, wherein the gripping tab of the port cap extends toward a side of the frame in use.

40. The port cap according to claim 31, wherein the closure portion includes an indentation along the end from which the gripping tab extends.

* * * * *